United States Patent [19]

Saville

[11] Plant 4,840

[45] Apr. 20, 1982

[54] ROSE PLANT

[75] Inventor: F. Harmon Saville, Rowley, Mass.

[73] Assignee: Nor'East Miniature Roses, Inc., Rowley, Mass.

[21] Appl. No.: 189,171

[22] Filed: Sep. 22, 1980

[51] Int. Cl.[3] ..... A01H 5/00

[52] U.S. Cl. ..... Plt./10

[58] Field of Search ..... Plt./10

*Primary Examiner*—Robert E. Bagwill

*Attorney, Agent, or Firm*—Vincent G. Gioia

[57] ABSTRACT

A new red miniature rose of excellent form and substance which retains color upon aging.

1 Drawing Figure

The present invention relates to a new and distinct variety rose plant of the miniature rose class, which was originated by my crossing as seed parent the rose known as "Rise 'N Shine" and the rose known as "Sheri Anne" as pollen parent.

Among the novel characteristics possessed by this new variety which distinguish it from its parents and all other varieties of which I am aware are high centered, hybrid tea-like blooms of brilliant red coloring which is relatively constant from bud to open bloom stages. Asexual reproduction by budding of the new variety as performed in Essex County, Mass., shows that the foregoing and other distinguishing characteristics come true to form and are established and transmitted through succeeding propagations.

The new and improved rose variety which I have developed is a fine red miniature rose of substantially pure coloring which retains its good form and coloring until ½ to full open. Flowers are primarily singly-borne and delightfully displayed on long stems.

The accompanying drawing shows typical specimens of the vegetative growth and flowers of the new variety in different stages of development and as depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "46A" is plate 46A of the Royal Horticultural Society Color Chart.

Parentage: Seedling.
*Seed parent.*—"Rise 'N Shine".
*Pollen parent.*—"Sheri Anne".
Class: Miniature.

The following observations are made of specimens grown in Essex County, Mass., during the month of July.

FLOWER

Blooming habit: Near continuous.

A. Bud:
(1) *Size.*—Small.
(2) *Form.*—High centered, hybrid tea-like.
(3) *Color.*—When sepals first divide — Currant Red 46A.

(4) *Sepals.*—Smooth, slightly foliated, longer than bud.
(5) *Peduncle.*—Length — good proportion to bloom. Aspect — straight. Strength — erect, strong. Color — 144B.

B. Bloom:
(1) *Size.*—Average size when fully expanded — about 1 to 1¼ inches.
(2) *Borne.*—Primarily singly, occasional sprays.
(3) *Form.*—High centered, petals reflex to points.
(4) *Petalage.*—Number of petals under normal conditions — about 20 to 25.
(5) *Color (during first two days).*—The predominant color seen as sepals unfurl is 46A to B. The reverse surface (petal underside) shows substantially the same coloring. As the bloom opens, the brilliant red coloring is retained, ranging from 46B to near 44A when fully open. Petals at point of attachment are near 12B.

C. Petals:
(1) *Texture.*—Thick, good substance.
(2) *Appearance.*—Inside — satiny; outside — satiny.
(3) *Form.*—Usually rounded until reflexing to star-like points.
(4) *Arrangement.*—Shingle-like.
(5) *Petaloids in center.*—Few.
(6) *Persistence.*—Drop cleanly.
(7) *Fragrance.*—Slight.
(8) *Lasting quality.*—Last well on plant and as cut flower.

REPRODUCTIVE ORGANS

A. Stamens, filaments and anthers:
(1) *Arrangement.*—Stamens regularly arranged around styles.
(2) *Color.*—22A.

B. Pollen:
*Color.*—163A.

C. Styles: Even, medium length.

D. Stigmas:
*Color.*—10C.

E. Hips: Globular, small, color 30A when mature, seeds do not protrude.

PLANT

A. Form: Upright, compact, bushy.

B. Growth: Very vigorous, uniform branching.
*Height attained.*—10 to 14 inches.

C. Foliage: Compound 5 to 7 leaflet leaves.
(1) *Size.*—Medium.

(2) *Quantity.*—Abundant.

(3) *Color.*—New and old foliage: upper side — 137A; under side — 138B.

(4) *Shape.*—Ovate.

(5) *Texture.*—Upper side — glossy; under side — matte.

(6) *Edge.*—Serrated.

(7) *Serration.*—Regular.

(8) *Leaf stem.*—Color — near to 146B; under side — near to 146C.

(9) *Stipules.*—Long, with short points.

(10) *Resistance to disease.*—Blackspot — average. Mildew — average.

D. Wood:

(1) *New wood.*—Color — near 146C. Bark — smooth.

(2) *Old wood.*—Color — near to 148A. Bark — smooth.

E. Thorns:

(1) *Thorns.*—Quantity — average. On laterals from stalk — few. Form — long, thin, pointed. Length — relatively long. Color (when young) — 184A. Position — irregular.

(2) *Prickles.*—None.

F. Winter hardiness: Needs some protection in extreme climate.

I claim:

1. A new and distinct variety of rose plant of the miniature class, substantially as shown and described, characterized particularly by brilliant red, high centered blooms borne primarily singly to a stem on an upright, vigorous plant.

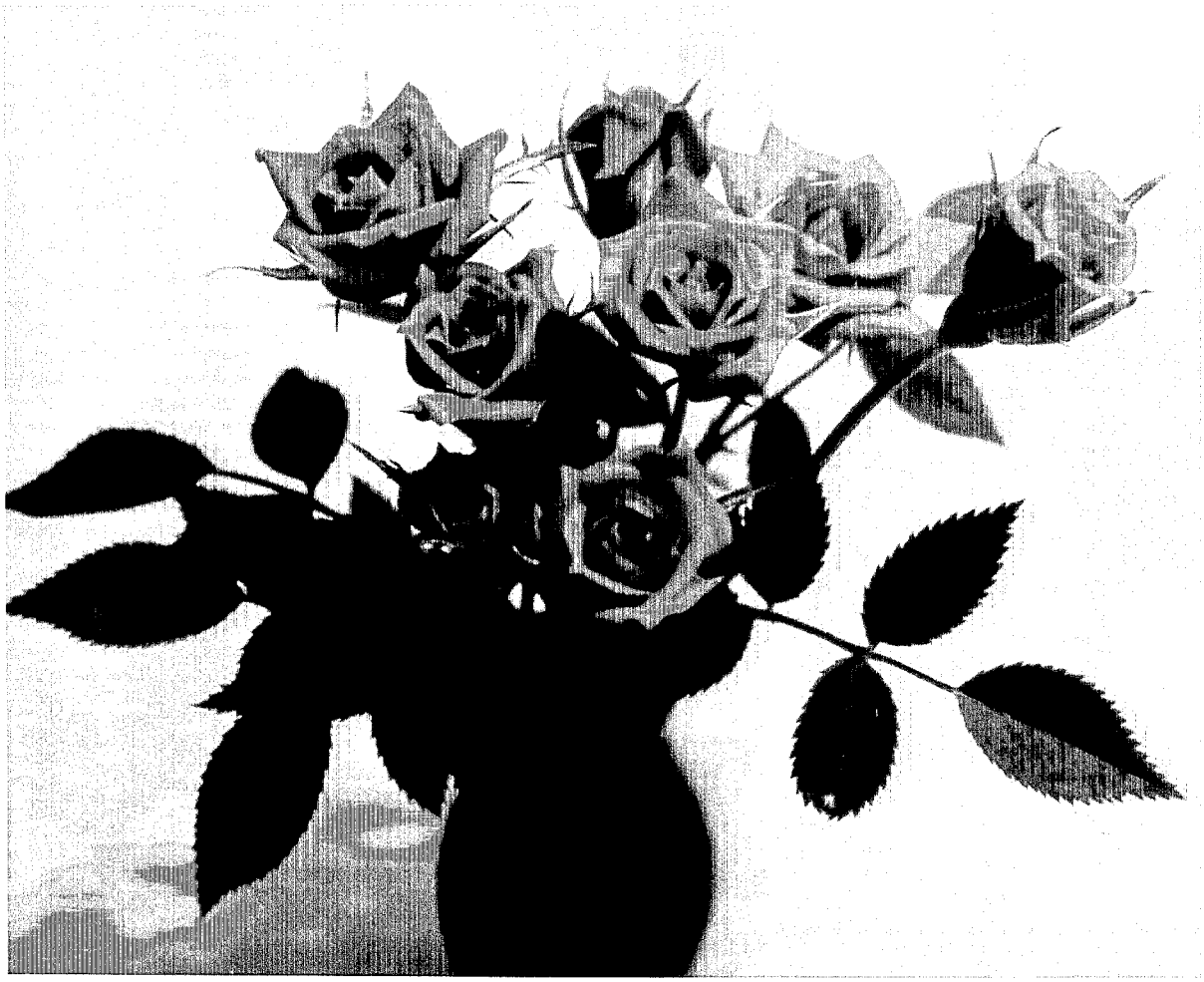

* * * * *